United States Patent [19]

Fravolini et al.

[11] Patent Number: 4,868,299
[45] Date of Patent: Sep. 19, 1989

[54] ANTIBACTERIALLY ACTIVE PYRIDO-BENZOTHIAZINE DERIVATIVES WITH LONG-TERM ACTION

[75] Inventors: Arnaldo Fravolini, Perugia; Patrizia Terni, Milan; Piergiuseppe Pagella, Isola S. Antonio, all of Italy

[73] Assignee: Mediolanum Farmaceutici Srl, Milan, Italy

[21] Appl. No.: 106,665

[22] Filed: Oct. 13, 1987

[30] Foreign Application Priority Data

Oct. 14, 1986 [IT] Italy ............................... 21999 A/86

[51] Int. Cl.[4] ............................................. C07D 513/04
[52] U.S. Cl. ....................................... 544/32; 540/575
[58] Field of Search .................... 540/575; 544/32; 514/218, 222, 225, 224.5

[56] References Cited

U.S. PATENT DOCUMENTS 4,668,784  5/1987  Mascellani et al. ................... 544/32
4,684,647  8/1987  Mascellani et al. ................... 544/32

Primary Examiner—John M. Ford
Attorney, Agent, or Firm—Arnold, White & Durkee

[57] ABSTRACT

The invention relates to antibacterially active pyrido-benzothiazine derivatives with long-term action, having the following general formula:

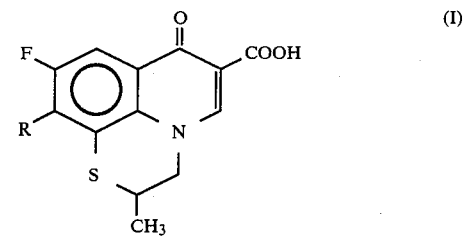

in which R is

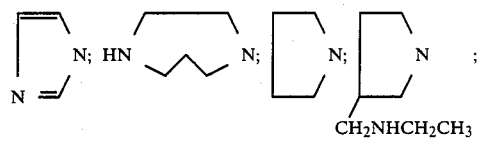

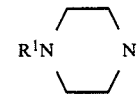

Where $R^1$ is H, $C_1$-$C_6$ alkyl, p-fluorophenyl, m-fluorophenyl, o-fluorophenyl or 2-pyridyl; or

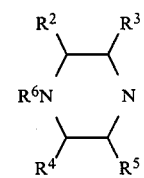

where $R^2$, $R^3$, $R^4$, $R^5$, $R^6$ are lower alkyls.

The invention also comprises the process for preparing compounds of general formula (I). Said process consists of a synthesis cycle using 2,4-difluoro-3-chloronitrobenzene and thiolactic acid as starting substances.

The inventiona also comprises pharmaceutical compositions containing at least one of the compounds of general formula (I) as active principle.

11 Claims, No Drawings

ANTIBACTERIALLY ACTIVE PYRIDO-BENZOTHIAZINE DERIVATIVES WITH LONG-TERM ACTION

This invention relates to a new class of highly antibacterially active pyrido-benzothiazine derivatives with long-term action, their preparation process and the pharmaceutical compounds which contain them.

Said pyrido-benzothiazine derivatives have the following general formula:

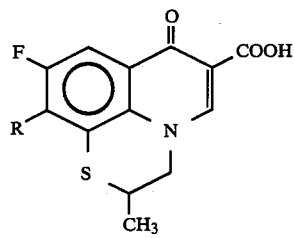

in which R is

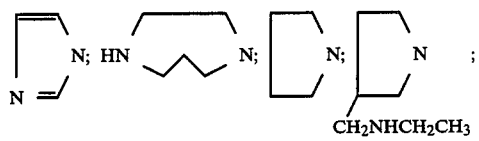

where $R^1$ is H, $C_1$–$C_6$ alkyl, p-fluorophenyl, m-fluorophenyl, o-fluorophenyl or 2-pyridyl; or

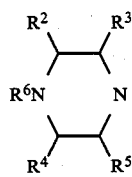

where $R^2$, $R^3$, $R^4$, $R^5$, $R^6$ are lower alkyls.

The derivatives according to the invention have a wide and powerful antibacterial activity which is substantially higher than most of the antibacterial compounds known up to the present time, both against gram-positive bacteria and against gram-negative bacteria. They are also rapidly absorbed after oral administration to reach high tissue levels, and their action is long-term such as to require only a single daily administration in systemic infections, and a single administration in surgical prophylaxes and urinary infections.

The process for preparing the pyrido-benzothiazine derivatives according to the present invention is based on a first reaction cycle by which, starting from 2,4-difluoro-3-chloronitrobenzene and thiolactic acid, ethyl 9-fluoro-10-chloro-2-methyl-7-oxo-2,3-dihydro-7H-pyrido[1,2,3-de][1,4]benzothiazine-1-sulphoxide-6-carboxylate (II) is prepared:

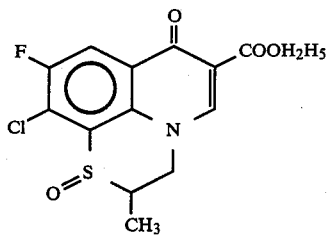

The Cl of this compound is then subjected to nucleophilic substitution with piperazine or N-methylpiperazine or pyrrolidine, the sulphoxide is reduced to thioether and finally the ester is hydrolysed to obtain the corresponding carboxylic acid of general formula (I).

The first reaction cycle, for preparing compound (II), is implemented in accordance with the following schema 1:

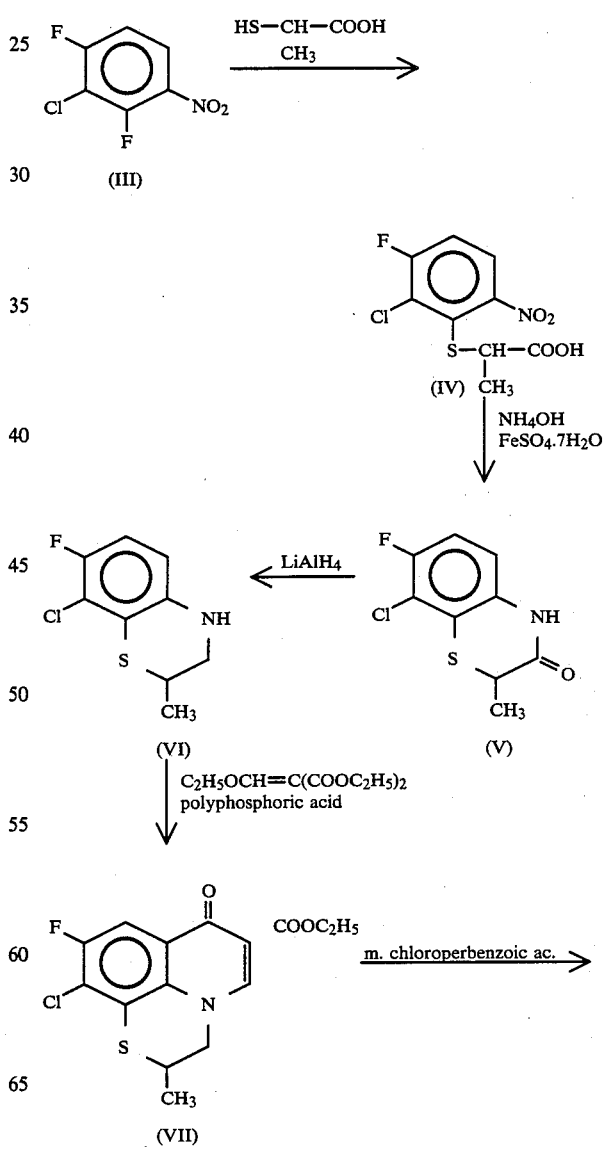

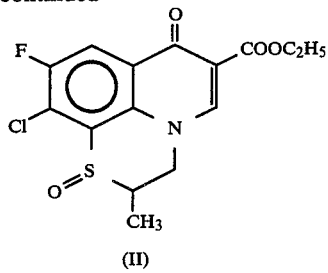

The compounds of general formula (I) are obtained from the compound (II) by the reactions represented by the following scheme 2:

The compound (V) is reacted with LiAlH₄ in a reaction medium consisting of anhydrous tetrahydrofuran at ambient temperature.

By flash chromatography purification, 8-chloro-7-fluoro-2-methyl-3,4-dihydro-2H-1,4-benzothiazine (VI) is obtained in the form of an oily product.

The compound (VI) is reacted firstly with ethyl ethoxymethylene malonate at a temperature of between 100° and 150° C., and then with polyphosphoric acid at a temperature of between 170° and 200° C.

By crystallisation from methyl alcohol, ethyl 9-fluoro-10-chloro-2-methyl-7-oxo-2,3-dihyrdo-7H-pyrido[1,2,3-de][1,4]benzothiazine-6-carboxylate (VII) is obtained.

The compound (VII) is reacted with m.chloroperbenzoic acid in a reaction medium consisting of ethyl

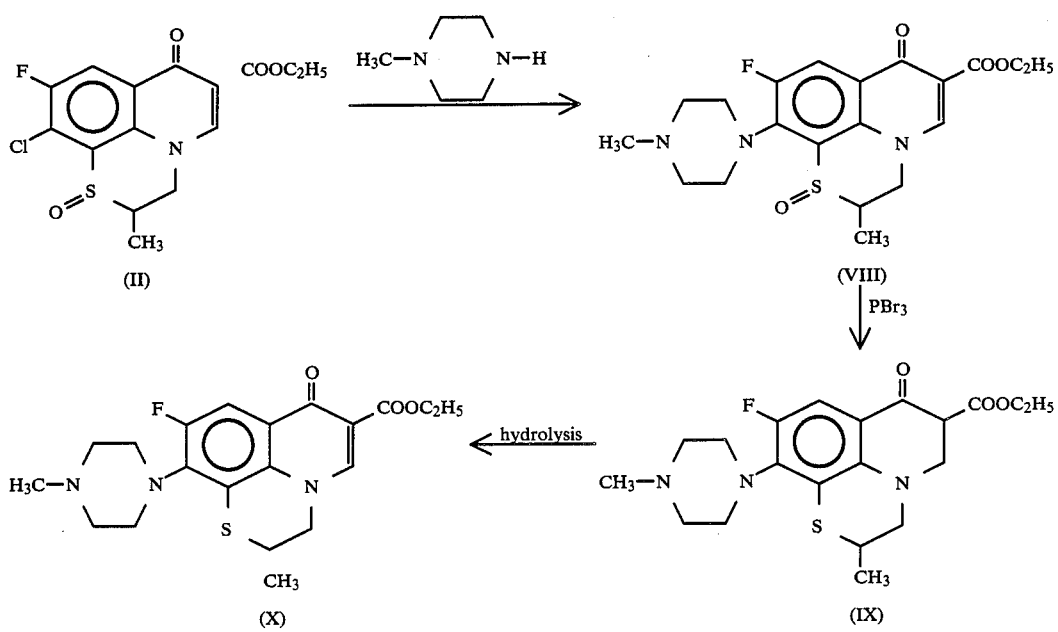

The compound (X) is a compound included within the general formula (I) in which R is

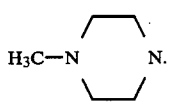

Operating in accordance with scheme 1 and reacting compound (II) with the respective amine, the compounds described in Examples 2 to 9 are obtained.

The reactions of scheme 1 are implemented by operating under the following conditions.

The 2,4-difluoro-3-chloro-nitrobenzene (III) in a dimethylsulphoxide and ethyl alcohol solution is reacted with thiolactic acid in aqueous alkaline solution at a temperature of between ambient and 100° C. By acidification with HCl and extraction, the nitroacid (IV) is obtained in the form of an oily product. The nitroacid (IV) is dissolved in a concentrated NH₄OH solution and reacted with a FeSO₄. 7H₂O solution at a temperature of between ambient with 50° C. After acidification with HCl, the benzothiazine derivative (V) separates in crystalline form.

alcohol at ambient temperature to give ethyl 9-fluoro-10-chloro-2-methyl-7-oxo-2,3-dihydro-7H-pyrido[1,2,3-de][1,4]benzothiazine-1-sulphoxide-6-carboxylate (II).

The following the procedure shown in scheme 2, the compound (II) is reacted with methylpiperazine in a reaction medium consisting of dimethylformamide at a temperature of between 90° and 110° C. to obtain ethyl 9-fluoro-10[N(N'-methyl)piperazinyl]-2-methyl-7-oxo-2,3-dihydro-7H-pyrido[1,2,3-de][1,4]benzothiazine-1-sulphoxide-6-carboxylate (VIII).

The compound (VIII) on treatment with PBr₃-dimethylformamide at ambient temperature produces ethyl 9-fluoro-10[N(N'-methyl)piperazinyl]-2-methyl-7-oxo-2,3-dihydro-7H-pyrido[1,2,3-de][1,4]benzothiazine-6-carboxylate (IX).

The compound (IX) is finally subjected to alkaline hydrolysis to obtain 9-fluoro-10[N(N'methyl)-piperazinyl]-2-methyl-7-oxo-2,3-dihydro-7H-pyrido[1,2,3-de][1,4]benzothiazine-6-carboxylic acid (X).

Operating in accordance with scheme 2, and reacting (II) with piperazine, 9-fluoro-10-[N-piperazinyl]-2-methyl-7-oxo-2,3-dihydro-7H-pyrido[1,2,3-de][1,4]benzothiazine-6-carboxylic acid (XI):

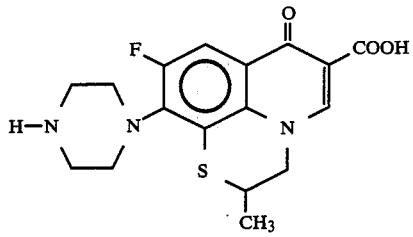

is obtained.

Again operating in accordance with scheme 2 and reacting (II) with pyrrolidine, 9-fluoro-10[N-pyrrolidinyl]-2-methyl-7-oxo-2,3-dihydro-7H-pyrido[1,2,3-de][1,4]benzothiazine-6-carboxylic acid (XII):

(XII)

is obtained.

The compounds of this invention can form salts by the addition of inorganic or organic acids such as hydrochloric, hydrobromic or methanesulphonic acid or the like, and can also form the corresponding carboxylates by treatment with sodium or potassium hydroxide. Consequently these compounds can be administered either orally, by injection or by external application, using the most suitable pharmaceutical forms prepared by known means.

The antibacterial activity of the compounds according to the invention was determined "in vitro" on pathogenic strains of recent clinical isolation by testing agar dilutions using a multipoint inoculator (Denley Techn. Ltd., England).

The culture medium used is isosensitest agar (Oxoid), in a quantity of 20 ml in a Petri capsule. The compounds to be tested were dissolved at various dilutions and incorporated in agar.

The bacterial inoculum, originating from an overnight broth and containing $10^5$ colony-forming units per point, was inoculated by a multipoint inoculator. The bacterial growth was evaluated after 18 hours of incubation at 37° C. The lowest concentration of the compound under examination able to completely inhibit growth was taken as the minimum inhibiting concentration (MIC).

The results relative to the antibacterial activity of the compounds described in the present invention are summarized in Table 1 and show that the compounds possess a powerful and wide antibacterial activity against gram positive and gram negative micro-organisms. For comparison purposes, the results relative to compound (XIII) and to nalidixic acid are also reported.

TABLE 1

IN-VITRO ANTIBACTERIAL ACTIVITY
Minimum Inhibiting Concentration (MIC) (μg/ml)

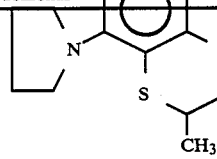

| MICROORGANISM | | (XIII) | COMPOUND (X) | COMPOUND (XI) | COMPOUND (XII) | NALIDIXIC ACID |
|---|---|---|---|---|---|---|
| Staphylococcus | 7 | 0.12 | 2 | 1 | 0.25 | >25 |
| Staphylococcus | 29 | 0.12 | 2 | 1 | 0.25 | >25 |
| Escherichia | 15 | 0.25 | 0.25 | 0.12 | 2 | 3.12 |
| Escherichia | 963 | 16 | 2 | 2 | 16 | >25 |
| Enterobacter | 041 | 0.12 | 0.25 | 0.12 | 2 | 3.12 |
| Enterobacter | 2653 | 0.12 | 0.5 | 0.25 | 16 | 1.56 |
| Klebsiella | 4 | 0.12 | 0.25 | 0.25 | 2 | 3.12 |
| Serratia | 9 | >32 | 8 | 8 | 16 | >25 |
| Serratia | 10 | 0.25 | 2 | — | 2 | — |
| Proteus | 25 | >32 | 8 | 4 | 2 | 12.5 |
| Proteus | 966 | >32 | 8 | 4 | 2 | >25 |
| Citrobacter | 118 | 1 | 0.5 | 0.5 | 16 | 12.5 |
| Citrobacter | 120 | >32 | 0.25 | 0.5 | 2 | 12.5 |
| Pseudomonas | 22437 | >32 | 16 | 16 | 16 | >25 |
| Pseudomonas | 19 | >32 | 16 | 16 | 2 | >25 |

The compound (X) was administered orally at a dose of 50 mg/kg to the rat after which the plasma, tissue and urine concentrations were evaluated by the HPLC method, as described hereinafter.

The urine was collected at various times during the 24 hours following administration. The results relative to urine concentrations are summarised in Table 2, and refer to a urine pool obtained form 6 female rates having a weight of about 100 g.

TABLE 2

| URINE CONCENTRATIONS OF COMPOUND (X) | | | |
|---|---|---|---|
| Hours after treatment | Volume excreted (ml) | Concentration (μg/ml) | Cumulative excretion (mg) |
| 0–1 | 5.5 | 90 | 0.50 |
| 1–2 | 3.2 | 260 | 1.33 |
| 2–4 | 7.2 | 100 | 2.05 |
| 4–8 | 6.0 | 180 | 3.13 |

TABLE 2-continued

URINE CONCENTRATIONS OF COMPOUND (X)

| Hours after treatment | Volume excreted (ml) | Concentration (μg/ml) | Cumulative excretion (mg) |
|---|---|---|---|
| 8–24 | 28.0 | 180 | 8.17 |

The percentage urine excretion of the non-metabolized product within 24 hours was about 27% of the orally administered dose. The urine concentrations were also found to be lasting and high.

The plasma and tissues (heart, kidney and liver) were withdrawn from groups of 3 female rats at various times after oral administration.

The results relative to plasma and tissue concentrations are summarised in Table 3, and show that the compound is rapidly absorbed after oral administration to induce high tissue levels. The concentrations relative to the heart, kidney and liver are always greater than those observed in the plasma and demonstrate that the compound possesses an excellent tissue bioavailability. In addition, high concentrations relative to the MIC values are still present 15 hours after administration.

TABLE 3

PLASMA AND TISSUE CONCENTRATIONS OF COMPOUND (X)

| Hours after treatment | Concentration μg/g (μg/ml for plasma) | | | |
|---|---|---|---|---|
| | Plasma | Heart | Kidney | Liver |
| 0.5 | 10.20 ± 1.19 | 19.17 ± 1.88 | 34.43 ± 2.55 | 62.93 ± 6.20 |
| 4 | 8.10 ± 1.02 | 18.63 ± 2.34 | 38.70 ± 2.44 | 34.33 ± 2.25 |
| 15 | 3.50 ± 0.76 | 4.63 ± 0.95 | 5.90 ± 1.32 | 9.37 ± 1.73 |

Operating in accordance with the described procedures, tests were also carried out with compounds (XI) and (XII). The results obtained were analogous to the tests carried out with compound (X).

The results of the described tests show that the compounds pertaining to the new pyridobenzothiazine series according to the invention have a wide spectrum of antibacterial activity and possess excellent pharmacokinetic characteristics.

The tissue and urine levels are particularly high and lasting, and it is therefore reasonable to assume a prolonged reaction which makes a single daily administration possible.

The HPLC determination was made by the following procedure: 2 mg of N-dimethyldiarepam (internal standard), 1 ml of citrate buffer (0.1 M, pH 6.2) and 6 ml of chloroform are added to 1 ml of plasma or to 1 ml of supernatant obtained after centrifuging a homogenized tissue in 3 volumes of physiological solution at 2000 r.p.m. for 5 minutes.

After agitating for 20 minutes and centrifuging at 3000 r.p.m. for 5 minutes, the organic phase is separated and dried over a water bath at 70° C.

The residue is collected in 50 μl of methanol, and 20 μl of the solution are injected into a HPLC (Gilson) column under the following conditions: column μ Bondopak C-18 (water, wavelength 245 nm), flow: 0.7 ml/min, mobile phase: (A) 0.1% acetic acid and (B) methanol, gradient:

| time | B % |
|---|---|
| 0 | 60 |

-continued

| time | B % |
|---|---|
| 10 min | 70 |
| 18 min | 60 |

The following examples are given for non-limiting illustration of the process for preparing the compounds of formula (I).

EXAMPLE 1

Preparation of 9-fluoro-10[N(N'-methyl)piperazinyl]-2-methyl-7-oxo-2,3-dihydro-7H-pyrido[1,2,3-de][1,4]benzothiazine-6-carboxylic acid (X)

(a) Preparation of the nitroacid (IV)

A solution of 1.1 g of thiolactic acid in 10 ml of $H_2O$ containing 0.8 g of NaOH is dripped into a solution of 2.8 g of 2,4-difluoro-3-chloronitrobenzene (III) in 20 ml of dimethylsulphoxide and 10 ml of ethyl alcohol. The mixture is kept under agitation overnight at ambient temperature, it is heated to 80° C. for 3 hours and then poured into water and filtered. The filtrate is firstly acidified with HCl and is then extracted with ethyl acetate. The organic phase is treated with an $Na_2CO_3$ solution and then acidified and extracted with $CHCl_3$. The extract is dried over $Na_2SO_4$ and the solvent is eliminated by evaporation. 1.9 g of the nitroacid (IV) are obtained in the form of an orange-coloured oil.

$^1$H-NMR (CDCl$_3$) δ: 1.47 (3H, d, CHCH$_3$); 3.98 (1H, q, CHCH$_3$); 7.08–7.68 (2H, m, aromatics).

(b) Preparation of the benzothiazinone derivative (V)

A solution of 48.7 g of FeSO$_4$.7H$_2$O dissolved in the minimum quantity of H$_2$O is added under agitation to a solution obtained by dissolving 7.4 g of the nitroacid (IV) in 100 ml of concentrated NaOH. The mixture is kept under agitation for one hour at ambient temperature and then for half hour at 40° C. It is filtered under vacuum and the precipitate washed on the filter with an aqueous ammonia solution. On acidifying the filtrate with HCl, a dirty-white crystalline product precipitates and is recrystallised for ethyl alcohol. 3.2 g of (V) are thus obtained, having a M.P. of 198°–200° C.

$^1$H-NMR (DMSO) δ: 1.38 (3H, d, CHCH$_3$); 3.73 (1H, q, CHCH$_3$); 6.72–7.35 (2H, m, aromatics); 11 (1H, wide s, NH)

(c) Preparation of 8-chloro-7-fluoro-2-methyl-3,4-dihyrdo-1,4-benzothiazine (VI)

A solution of 2.3 g of (V) in 50 ml of anhydrous tetrahydrofuran is added to a suspension of 0.7 g of LiAlH$_4$ in 10 ml of anhydrous tetrahydrofuran, at ambient temperature. The mixture is kept under agitation for half hour, filtered and the filtrate alkalized with a 10% NaOH solution.

The alkaline solution is extracted with CHCl$_3$, the chloroform extract is dried and the solvent evaporated. 1.8 g of an oil separates, and is purified by flash chromatography to give 0.9 g of (VI) in the form of a dark oily product.

$^1$H-NMR (CDCl$_3$) δ: 1.32 (3H, d, CHCH$_3$); 2.83–3.54 (3H, m, CHCH$_3$ and CH$_2$); 3.98 (1H, wide s, NH); 6.05–6.70 (2H, m, aromatics).

(d) Preparation of ethyl 9-fluoro-10-chloro-2-methyl-7-oxo-2,3-dihydro-7H-pyrido[1,2,3-de][1,4]benzothiazine-6-carboxylate (VII)

2.73 g of ethyl ethoxymethylenemalonate are added to 2.5 g of (VI) and the mixture heated in an oil bath of 120° C. for 2 hours and then to 180° C. for half hour.

On completion of the reaction, the temperature is reduced and at 80° C. 10 g of polyphosphoric acid are added, the temperature raised to 185° C. and maintained there until ethyl alcohol development ceases.

The reaction mixture is cooled and poured into $H_2O$ and ice. A solid brown product separates and is filtered off, washed with a dilute $Na_2CO_2$ solution and then with $H_2O$.

On crystallisation from methyl alcohol, 2.9 g of the product (VII) are obtained having a M.P. of 199°–201° C.

$^1$H-NMR (TFA) δ: 1.30–1.75 (6H, m, $CHCH_3$ and $CH_2CH_3$); 3.68–4.03 (1H, m, $CHCH_3$); 4.64 (2H, q, $CH_2CH_3$); 4.90–5.18 (2H, m, $CH_2$); 8.05 (1H, d, $J_{H-F}\simeq 7$ Hz, $C_8$-H); 9.13 (1H, s, $C_6$-H).

(e) Preparation of ethyl 9-fluoro-10-chloro-2-methyl-7-oxo-2,3-dihydro-7H-pyrido[1,2,3-de][1,4]benzothiazine-1-sulphoxide-6-carboxylate (II)

A solution of 2 g of m.chloroperbenzoic acid in 15 ml of ethyl alcohol is dripped at ambient temperature under agitation into a solution of 3 g of the product (VII) in 400 ml of ethyl alcohol.

The mixture is left under agitation for 2 hours at ambient temperature, 0.5 g of m.chloroperbenzoic acid are added and the mixture kept under agitation until the initial substance disappears.

0.8 g of the sulphoxide (II) separate and are recovered by filtration and crystallisation from ethyl alcohol (M.P. 292°–293° C.).

By concentrating the filtrate, 1 g of a crystalline product is collected having a M.P. of 202°–204° C., consisting of a mixture of the two sulphoxide enantiomers (II). This mixture can be used as such for the subsequent reactions.

$^1$H-NMR (DMSO) δ: 0.98 (3H, d, $CHCH_3$); 1.30 (3H, t, $CH_2CH_3$); 3.58–3.90 (1H, m, $CHCH_3$); 4.21 (2H, q, $CH_2CH_3$); 4.50–4.70 (2H, m, $CH_2$); 8.18 (1H, d, $J_{H-F}\simeq 9$ Hz, $C_8$-H); 8.63 (1H, s, $C_6$-H).

(f) Preparation of ethyl 9-fluoro-10-[N(N'-methyl)piperazinyl]-2-methyl-7-oxo-2,3-dihydro-7H-pyrido[1,2,3-de][1,4]benzothiazine-1-sulphoxide-6-carboxylate (VIII)

A solution of 1.45 g of (II) in 10 ml of dimethylformamide to which 2 g of methylpiperazine has been added is heated in an oil bath to 100° C. for one hour, the solvent distilled off under vacuum and the pitch-like residue chromatographed through silica gel and eluted with $CHCl_3$. 0.780 g of the solid product (VIII) are obtained having a M.P. of 235°–237° C.

$^1$H-NMR (CDCL$_3$) δ: 1.08 (3H, d, $CHCH_3$); 1.40 (3H, t, $CH_2CH_3$); 2.40 (3H, s, $CH_3N$-$CH_3$); 2.52–2.82 (8H, m, piperazinic H); 4.02–4.12 (1H, m, $CHCH_3$); 4.35 (2H, q, j=6 Hz, $CH_2CH_3$); 4.78–5.02 (2H, m, $CH_2$); 8.25 (1H, d, $J_{H-F}\simeq 12$ Hz, $C_8$-H); 8.42 (1H, s, $C_6$-H).

(g) Preparation of ethyl 9-fluoro-10-[N(N'-methyl)piperazinyl]-2-methyl-7-oxo-2,3-dihydro-7H-pyrido[1,2,3-de][1,4]benzothiazine-6-carboxylate (IX)

0.2 g of (VII) are suspended in 3 ml of dimethylformamide, 0.150 g of $PBr_3$ are added at ambient temperature and the mixture allowed to react for 2 hours while maintaining this temperature.

The solvent is removed by vacuum distillation to obtain a solid pitch-like residue represented by (IX).

(h) Preparation of 9-fluoro-10-[N(N'-methyl)piperazinyl]-2-methyl-7-oxo-2,3-dihydro-7H-pyrido[1,2,3-de][1,4]benzothiazine-6-carboxylic acid (X)

3 ml of 10% aqueous NaOH solution and 2 ml of ethyl alcohol are added to the pitch-like solid obtained from step (g).

The mixture is heated under reflux for 20 minutes, and is then concentrated to one half its volume with the result that a yellow-green solid precipitates, this being collected and washed with a little water obtain 0.136 g of the product (X) which when crystallised from dimethylformamide and $H_2O$ has a M.P. of 328°–330° C.

$^1$H-NMR (DMSO+$D_2O$) δ: 1.40 (3H, d, $CHCH_3$); 2.90 (3H, s, N-$CH_3$); 3.22–3.52 (8H, m, piperazinic H); 4.05–4.40 (1H, m, $CHCH_3$); 4.56–4.82 (2H, m, $CH_2$); 7.56 (1H, d, $J_{H-F}\simeq 12$ Hz, $C_8$-H); 8.60 (1H, s, $C_6$-H).

EXAMPLE 2

Preparation of 9-fluoro-10[N-piperazinyl]-2-methyl-7-oxo-2,3-dihydro-7H-pyrido[1,2,3-de][1,4]benzothiazine-6-carboxylic acid (XI)

The steps (a) to (e) of Example 1 are repeated to obtain the compound (II).

0.9 g of the compound (II) are suspended in 5 ml of dimethylformamide and 1 g of piperazine added. The mixture is heated to 100° C. in an oil bath for one hour, the solvent eliminated by vacuum distillation and the residual pitch-like mass purified by silica gel chromatography.

0.8 g of oil are obtained and taken up in 3 ml of dimethylformamide, to which 0.7 g of $PBr_3$ are then added dropwise under agitation. The mixture is kept under agitation at ambient temperature for one hour and the solvent then eliminated under vacuum. A pitch-like product is obtained which, when taken up in methyl alcohol, gives 0.7 g of a solid product having a M.P. of 301°–305° C. 3 ml of 10% NaOH and 2 ml of ethyl alcohol are added to 0.5 g of this product and the mixture heated under reflux for one hour. The reaction mixture is diluted with $H_2O$ and ice and is then acidified with HCl. A light brown product precipitates which when washed with water gives 0.360 g of solid having a M.P. of 329°–330° C. On crystallisation from aqueous acetic acid, pure (X) is obtained having a M.P. of 331°–332° C.

$^1$H-NMR (TFA) δ: 1.58 (3H, d, $CHCH_3$); 3.42–3.86 (8H, m, piperazinic H); 4.35–4.74 (1H, m, $CHCH_3$); 4.80–5.10 (2H, $CH_2$); 7.94 (1H, d, $J_{H-F}\simeq 12$ Hz, $C_8$-H); 9.10 (1H, s, $C_6$-H).

EXAMPLE 3

Preparation of 9-fluoro-10[N-pyrrolidine]-2-methyl-7-oxo-2,3-dihydro-7H-pyrido[1,2,3-de][1,4]benzothiazine-6-carboxylic acid (XII)

Steps (a) to (e) of Example 1 are repeated to obtain the compound (II).

1.3 g of compound (II) are suspended in 7.0 ml of dimethylformamide, 1.28 g of pyrrolidine are added and the mixture is heated in an oil bath to 120° C. for one hour.

It is then left at ambient temperature for 12 hours, after which the solvent is distilled off under vacuum to obtain a pitch-like product which on treatment with ethyl alcohol gives 1 g of ethyl 9-fluoro-10[1-pyrrolidine]-2-methyl-7-oxo-2,3-dihydro-7H-pyrido[1,2,3-de][1,4]benzothiazine-1-sulphoxide-6-carboxylate having a M.P. of 230°–232° C.

$^1$H-NMR (TFA) δ: 1.50 (3H, t, CH$_2$CH$_3$); 1.66 (3H, d, CHCH$_3$); 1.92–2.38 (4H, m, CH$_2$-CH$_2$); 3.4–3.38 (1H, m, CHCH$_3$); 3.90–4.40 (4H, m, CH$_2$NCH$_2$); 4.6 (2H, q, CH$_2$CH$_3$); 4.51–5.50 (2H, m, NCH$_2$CH); 8.10 (1H, d, $J_{H-F}$≃12 Hz, C$_8$-H); 9 (1H, s, C$_6$-H).

0.950g of the compound obtained are suspended in 10 ml of dimethylformamide, after which 0.85 g of PBr$_3$ are added dropwise while cooling with ice, the mixture then being left at ambient temperature under agitation for 3 hours after which the solvent is evaporated under vacuum.

The residual pitch-like mass is suspended in 10 ml of 10% NaOH and 2 ml of ethyl alcohol and the suspension heated under reflux until complete dissolution, after which the solution is poured into H$_2$O and ice and then acidified with HCl. On washing with H$_2$O 0.620 g of a product having a M.P. of 258°–260° C. are obtained, and which on crystallisation from acetic acid gives the pure compound (XII) having a M.P. of 267°–268° C.

$^1$H-NMR (TFA) δ: 1.70 (3H, d, CHCH$_3$); 2.4–2.78 (4H, m, CH$_2$-CH$_2$); 4.05–4.40 (4H, m, CH$_2$NCH$_2$); 4.50–4.96 (1H, m, CHCH$_3$); 5.00–5.32 (2H, m, NCH$_2$CH); 8.30 (1H, d, $J_{H-F}$≃12 Hz, C$_8$-H); 9.32 (1H, s, C$_6$-H).

The compounds of the following examples were synthesized by methods similar to those described in Examples 2 and 3:

EXAMPLE 4

9-fluoro-10-[N-homopiperazinyl]-2-methyl-7-oxo-2,3-dihydro-7H-pyrido[1,2,3-de][1,4]benzothiazine-6-carboxylic acid; crystallisation solvent: AcOH/H$_2$O;

M.P. 320°–321° C.

$^1$H-NMR (TFA) δ: 1.63 (3H, d, J≃6 Hz, CHCH$_3$); 3.33–4.10 (11H, homopiperazinic CH$_2$ and CHCH$_3$); 4,40–5.10 (2H, m, CH$_2$); 8.08 (1H, d, J≃12 Hz, C$_8$-H); 9.20 (1H, s, C$_6$-H).

EXAMPLE 5

9-fluoro-10[N-(3,5-dimethyl)-piperazinyl]-2-methyl-7-oxo-2,3-dihydro-7H-pyrido[1,2,3-de][1,4]benzothiazine-6-carboxylic acid; crystallisation solvent: DMF/H$_2$O;

M.P. 279°–282° C.

$^1$H-NMR (TFA) δ: 1.58 (6H, d, J≃6 Hz, piperazinic CH$_3$); 1.70 (3H, d, J≃6 Hz, CHCH$_3$); 3.45–4.14 (7H, m, CH and piperazinic CH$_2$ and CHCH$_3$); 4.56–5.28 (2H, m, CH$_2$); 8.20 (1H, d, J≃12 Hz, C$_8$-H); 9.10 (1H, s, C$_6$-H).

EXAMPLE 6

9-fluoro-10-(N-imidazolyl)-2-methyl-7-oxo-2,3-dihydro-7H-pyrido[1,2,3-de][1,4]benzothiazine-6-carboxylic acid;

M.P. 279°–282° C.

$^1$H-NMR (DMSO-d$_6$) δ: 1.38 (3H, d, J≃6 Hz, CHCH$_3$); 3.65–4.05 (1H, m, CHCH$_3$); 4.28–5.02 (2H, m, CH$_2$); 7.38–7.73 (2H, m, imidazolic H); 8.00 (1H, d, J≃10 Hz, C$_8$-H); 8.50 (1H, wide s, imidazolic H); 8.95 (1H, s, C$_6$-H).

EXAMPLE 7

9-fluoro-10-{N-[N'-(2-pyridyl)-]-piperazinyl}-2-methyl-7-oxo-2,3-dihydro-7H-pyrido[1,2,3-de][1,4]benzothiazine-6-carboxylic acid; crystallisation solvent: DMF;

M.P. 305°–308° C.

$^1$H-NMR (TFA) δ: 1.68 (3H, d, J≃6 Hz, CHCH$_3$); 3.50–4.15 (9H, m, piperazinic CH$_2$ and CHCH$_3$); 4.50–5.28 (2H, m, CH$_2$); 6.95–7.48 (2H, m, pyridinic H); 7.88–8.27 (3H, m, pyridinic H and C$_8$-H); 9.30 (1H, s, C$_6$-H).

EXAMPLE 8

9-fluoro-10-{N-[N'-(4-fluorophenyl)]-piperazinyl}-2-methyl-7-oxo-2,3-dihydro-7H-pyrido[1,2,3-de][1,4]benzothiazine-6-carboxylic acid;

crystallisation solvent: DMF.

M.P. 313°–315° C.

$^1$H-NMR (TFA) δ: 1.67 (3H, d, J≃6 Hz, CHCH$_3$); 3.52–4.40 (9H, m, piperazinic CH$_2$ and CHCH$_3$); 4.50–5.20 (2H, m, CH$_2$); 7.18–7.42 and 7.54–7.75 (each 2H, m, aromatic H); 8.10 (1H, d. J≃10 Hz, C$_8$-H); 9.20 (1H, s, C$_8$-H).

EXAMPLE 9

10{2-[ethylamino)methyl]-1-pyrrolidinyl}-9-fluoro-2-methyl-7-oxo-2,3-dihydro-7H-pyrido[1,2,3-de][1,4]benzothiazine-6-carboxylic acid crystallisation solvent: DMF/H$_2$O.

$^1$H-NMR (TRA) δ: 1.5 (3H, m, CH$_2$CH$_3$); 1.65 (3H, d, J≃6 Hz, SCHCH$_3$); 3.13–512 (14H, m, CH$_2$ and CHCH$_3$); 8.27 (1H, d, C$_8$-H J≃10.5 Hz); 9.4 (1H, s, C$_6$-H).

What is claimed:

1. Process for preparing a compound of the formula:

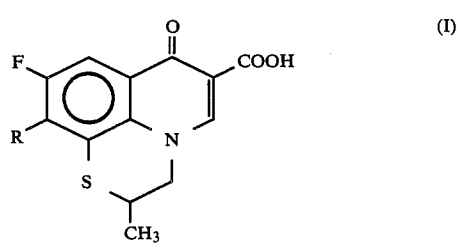

in which R is

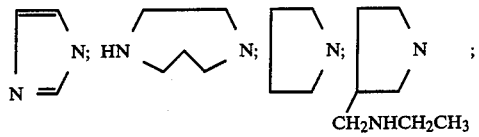

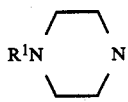

where $R^1$ is H, $C_1$–$C_6$ alkyl, p-fluorophenyl, m-fluorophenyl, o-fluorophenyl or 2-pyridyl; or

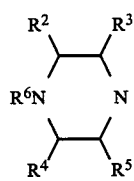

where $R^2$, $R^3$, $R^4$, $R^5$, $R^6$ are lower alkyls,
characterised in that using a first reaction cycle and starting from 2,4-difluoro-3-chloronitrobenzene (III) and thiolactic acid, ethyl 9-fluoro-10-chloro-2-methyl-7-oxo-2,3-dihydro-7H-pyrido [1,2,3-de][1,4]benzothiazine-1-sulphoxide-6-carboxylate (II) is prepared, and the Cl of this compound is then subjected to nucleophilic substitution with the respective amines, the sulphoxide group is reduced to a thioether group, and finally the ester is hydrolysed to obtain the corresponding carboxylic acid of general formula (I).

2. A process as claimed in claim 1, characterised in that the nitroacid (IV) obtained by reacting the 2,4-difluoro-3-chloronitrobenzene (III) with thiolactic acid is treated with FeSO$_4$.7H$_2$O to obtain the benzothiazinone derivative (V) from which, by reduction with LiAlH$_4$, the benzothiazine (VI) is obtained and this is treated with ethyl ethoxymethylenemalonate and then with polyphosphoric acid to give ethyl 9-fluoro-10-chloro-2-methyl-7-oxo-2,3-dihydro-7H-pyrido[1,2,3-de][1,4]benzothiazine-carboxylate (VII) from which the compound (II) is obtained by treatment with m.chloroperbenzoic acid.

3. A process as claimed in claim 2, characterised in that said reaction between (III) and thiolactic acid is implemented by treating a solution of (III) in dimethylsulphoxide and ethyl alcohol with an aqueous alkaline solution of thiolactic acid at a temperature of between ambient and 100° C.

4. A process as claimed in claim 2, characterised in that said treatment of the nitroacid (IV) with FeSO$_4$.7H$_2$O is conducted in a concentrated NH$_4$OH solution at a temperature of between ambient and 50° C.

5. A process as claimed in claim 2, characterised in that said treatment of the compound (V) with LiAlH$_4$ is conducted in a reaction medium consisting of anhydrous tetrahydrofuran at ambient temperature.

6. A process as claimed in claim 2, characterised in that the compound (VI) is treated firstly with ethyl ethoxymethylene malonate at a temperature of between 100° and 200° C. and then with polyphosphoric acid at a temperature of between 170° and 200° C.

7. A process as claimed in claim 2, characterised in that said treatment of the compound (VII) with m.chloroperbenzoic acid is implemented in a reaction medium consisting of ethyl alcohol at ambient temperature.

8. A process as claimed in claim 2, characterised in that said nucleophilic substitution of the Cl of compound (II) is implemented by treating this compound with said amines in a reaction medium consisting of dimethylformamide at a temperature of between 90° and 110° C.

9. A process as claimed in claim 1, characterised in that the reduction of said sulphoxide group is implemented by treatment with PBr$_3$ in a dimethylformamide environment at ambient temperature.

10. A process as claimed in claim 1, characterised in that said ester hydrolysis is implemented by treatment under boiling conditions with an aqueous NaOH solution.

11. A process for preparing a compound of formula:

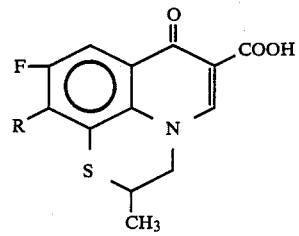

in which R is

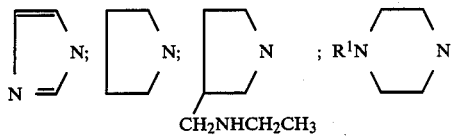

where $R^1$ is H, C–C$_6$ alkyl, p-fluorophenyl, m-fluorophenyl, o-fluorophenyl, 2-pyridyl, or 3,5-dimethyl-piperazine, which comprises:

(a) reacting 2,4-difluoro-3-chloronitrobenzene with thiolactic acid;

(b) reacting the obtained nitroacid with FeSO$_4$.7H$_2$O to produce the relevant benzothiazinone derivative;

(c) reducing the said benzothiazinone derivative to benzothiazine by means of LiAlH$_4$;

(d) reacting the benzothiazine with ethyl ethoxymethylenemalonate and then with polyphosphoric acid to give ethyl-9-fluoro-10-chloro-2-methyl-7-oxo-2,3-dihydro-7H-pyrido[1,2,3,-de][1,4]benzothiazine-6-carboxylate;

(e) reacting the carboxylate with m-chloroperbenzoic acid to give ethyl-9-fluoro-10-chloro-2-methyl-7-oxo-2,3,-dihydro-7H-pyrido[1,2,3,-de][1,4]benzothiazine-1-sulfoxide-6-carboxylate;

(f) reacting the sulfoxide-carboxylate with an amine selected from the group consisting of methylpiperazine, piperazine, pyrrolidine, 3,5-dimethylpiperazine, imidazoline, 2-pyridylpiperazine, fluorophenylpiperazine, (ethylamino)methyl-1-pyrrolidine;

(g) reducing the sulfoxide group to a thioether group and finally hydrolyzing the ester to the corresponding acid.

* * * * *